US010260338B2

(12) United States Patent
Smits

(10) Patent No.: US 10,260,338 B2
(45) Date of Patent: Apr. 16, 2019

(54) OPTICAL FLUID ANALYZER WITH CALIBRATOR AND METHOD OF USING SAME

(71) Applicant: Schlumberger Technology Corporation, Sugar Land, TX (US)

(72) Inventor: Anthony Smits, Yokohama (JP)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 259 days.

(21) Appl. No.: 13/905,136

(22) Filed: May 30, 2013

(65) Prior Publication Data

US 2014/0352397 A1 Dec. 4, 2014

(51) Int. Cl.
G01N 33/00 (2006.01)
G01N 21/27 (2006.01)
G01N 35/00 (2006.01)
G01N 33/28 (2006.01)
E21B 49/10 (2006.01)

(52) U.S. Cl.
CPC ........... *E21B 49/10* (2013.01); *G01N 21/274* (2013.01); *G01N 33/0006* (2013.01); *G01N 35/00594* (2013.01); *G01N 35/00693* (2013.01)

(58) Field of Classification Search
CPC .. G01N 21/00; G01N 33/0006; G01N 21/274; G01N 35/00693; G01N 35/00594; G01N 33/2823; G01N 2201/127
See application file for complete search history.

(56) References Cited

U.S. PATENT DOCUMENTS

| 7,241,115 B2* | 7/2007 | Luongo .................. F04B 51/00 340/605 |
| 7,458,252 B2 | 12/2008 | Freemark et al. |
| 7,788,972 B2 | 9/2010 | Terabayashi et al. |
| 2002/0178803 A1 | 12/2002 | Pelletier et al. |
| 2006/0005607 A1* | 1/2006 | Blumke .............. G01M 17/007 73/37 |

(Continued)

FOREIGN PATENT DOCUMENTS

WO    2009/009409    1/2009

OTHER PUBLICATIONS

International search report and written opinion for the equivalent PCT patent application No. PCT/US2014/040028 dated Oct. 1, 2014.

*Primary Examiner* — Daniel S Larkin
*Assistant Examiner* — Anthony W Megna Fuentes
(74) *Attorney, Agent, or Firm* — Eileen Pape

(57) ABSTRACT

A fluid analyzer for a downhole tool positionable in a wellbore penetrating a subterranean formation is provided. The fluid analyzer includes an optical sensor positioned in the downhole tool to receive a downhole fluid therefrom. The optical sensor includes an optical cell to measure properties of the downhole fluid in a flowline of the downhole tool, and has a wavelength range. The fluid analyzer also includes a calibration fluid having a liquid that absorbs outside of the wavelength range, and a calibrator. The calibrator includes a fluid source housing the calibration fluid and at least one valve. The fluid source is operatively connectable to the optical sensor to provide the calibration fluid thereto whereby the calibration fluid is measureable by and calibratable to the optical sensor.

16 Claims, 5 Drawing Sheets

(56) References Cited

U.S. PATENT DOCUMENTS

| | | |
|---|---|---|
| 2006/0175547 A1 | 8/2006 | Difoggio et al. |
| 2008/0093078 A1 | 4/2008 | Vasques et al. |
| 2011/0042071 A1 | 2/2011 | Hsu et al. |
| 2011/0061439 A1 | 3/2011 | Dong et al. |

* cited by examiner

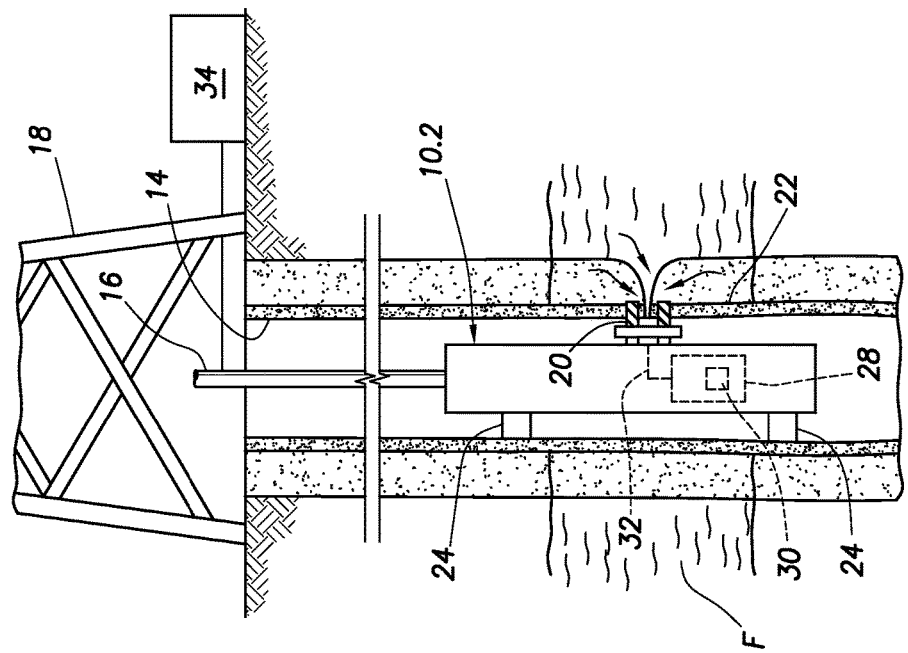
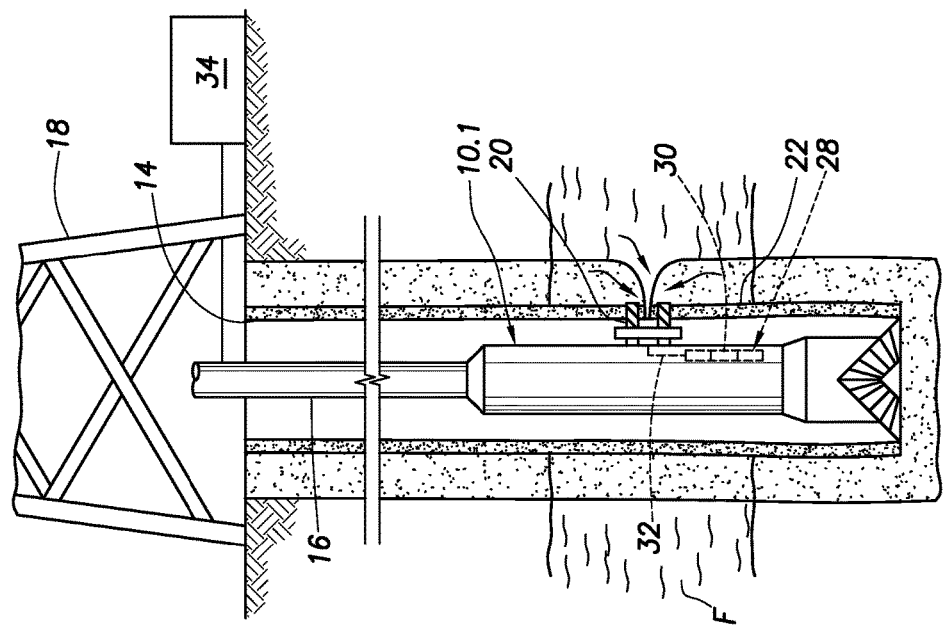
FIG.1.1
FIG.1.2

OPTICAL FLUID ANALYZER WITH CALIBRATOR AND METHOD OF USING SAME

BACKGROUND

The present disclosure relates generally to wellsite operations. In particular, the present disclosure relates to formation evaluation methods and apparatuses, and calibration thereof.

Wellbores are drilled to locate and produce hydrocarbons. A downhole drilling tool with a bit at an end thereof is advanced into the ground to form a wellbore. As the drilling tool is advanced, drilling mud is pumped through the drilling tool and out the drill bit to cool the drilling tool and carry away cuttings. The fluid exits the drill bit and flows back up to the surface for recirculation through the drilling tool. The drilling mud is also used to form a mudcake to line the wellbore.

During a drilling operation, various downhole evaluations may be performed to determine characteristics of the wellbore and surrounding formation. In some cases, the drilling tool may be provided with devices to test and/or sample the surrounding formation and/or fluid contained in reservoirs therein. In some cases, the drilling tool may be removed and a downhole wireline tool may be deployed into the wellbore to test and/or sample the formation. These samples or tests may be used, for example, to determine whether valuable hydrocarbons are present.

Formation evaluation may involve drawing fluid from the formation into the downhole tool for testing and/or sampling. Various devices, such as probes or packers, may be extended from the downhole tool to establish fluid communication with the formation surrounding the wellbore and to draw fluid into the downhole tool. Downhole tools may be provided with fluid analyzers and/or sensors to measure downhole parameters, such as fluid properties. Examples of downhole devices are provided in Patent/Publication Nos. U.S. Pat. No. 7,458,252, US2011/0061439, EP2179135, and WO2009/009409 the entire contents of which are hereby incorporated by reference herein.

SUMMARY

In one aspect, the present disclosure relates to a fluid analyzer for a downhole tool positionable in a wellbore penetrating a subterranean formation. A downhole fluid is receivable in a flowline of the downhole tool. The fluid analyzer includes an optical sensor positioned in the downhole tool to receive the downhole fluid therefrom. The optical sensor includes an optical cell to measure properties of the downhole fluid in the flowline, and has a wavelength range. The fluid analyzer also includes a calibration fluid having a liquid that absorbs outside of the wavelength range, and a calibrator. The calibrator includes a fluid source housing the calibration fluid and at least one valve. The fluid source is operatively connectable to the optical sensor to provide the calibration fluid thereto whereby the calibration fluid is measureable by the optical sensor and calibratable thereto.

In another aspect, the present disclosure relates to a downhole tool positionable in a wellbore penetrating a subterranean formation. The downhole tool includes a housing having a flowline receiving a downhole fluid therein and a fluid analyzer. The fluid analyzer includes an optical sensor positioned in the downhole tool to receive the downhole fluid therefrom. The optical sensor includes an optical cell to measure properties of the downhole fluid in the flowline, and has a wavelength range. The fluid analyzer also includes a calibration fluid having a liquid that absorbs outside of the wavelength range, and a calibrator. The calibrator includes a fluid source housing the calibration fluid and at least one valve. The fluid source is operatively connectable to the optical sensor to provide the calibration fluid thereto whereby the calibration fluid is measureable by the optical sensor and calibratable thereto.

In yet another aspect, the present disclosure relates to a method of calibrating a fluid analyzer of a downhole tool positionable in a wellbore penetrating a subterranean formation. A downhole fluid is receivable in a flowline of the downhole tool. The method involves providing the fluid analyzer with a calibrator including an optical sensor, a calibration fluid and a calibrator. The optical sensor is positioned in the downhole tool to receive the downhole fluid therefrom, includes an optical cell to measure properties of the downhole fluid in the flowline, and has a wavelength range. The calibration fluid includes a liquid that absorbs outside of the wavelength range. The calibrator includes a fluid source housing the calibration fluid and at least one valve. The fluid source is operatively connectable to the optical sensor to provide the calibration fluid thereto. The method also involves providing the calibration fluid to the fluid analyzer via the calibrator, and measuring the calibration fluid at a downhole location with the optical sensor.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

Embodiments of the optical fluid analyzers and the methods of using same are described with reference to the following figures. The same numbers are used throughout the figures to reference like features and components.

FIGS. 1.1 and 1.2 depict schematic views, partially in cross-section, of a wellsite with a downhole drilling tool and a downhole wireline tool, respectively, deployed into a wellbore for performing downhole formation evaluation in accordance with embodiments of the present disclosure;

DETAILED DESCRIPTION

Figure 2:
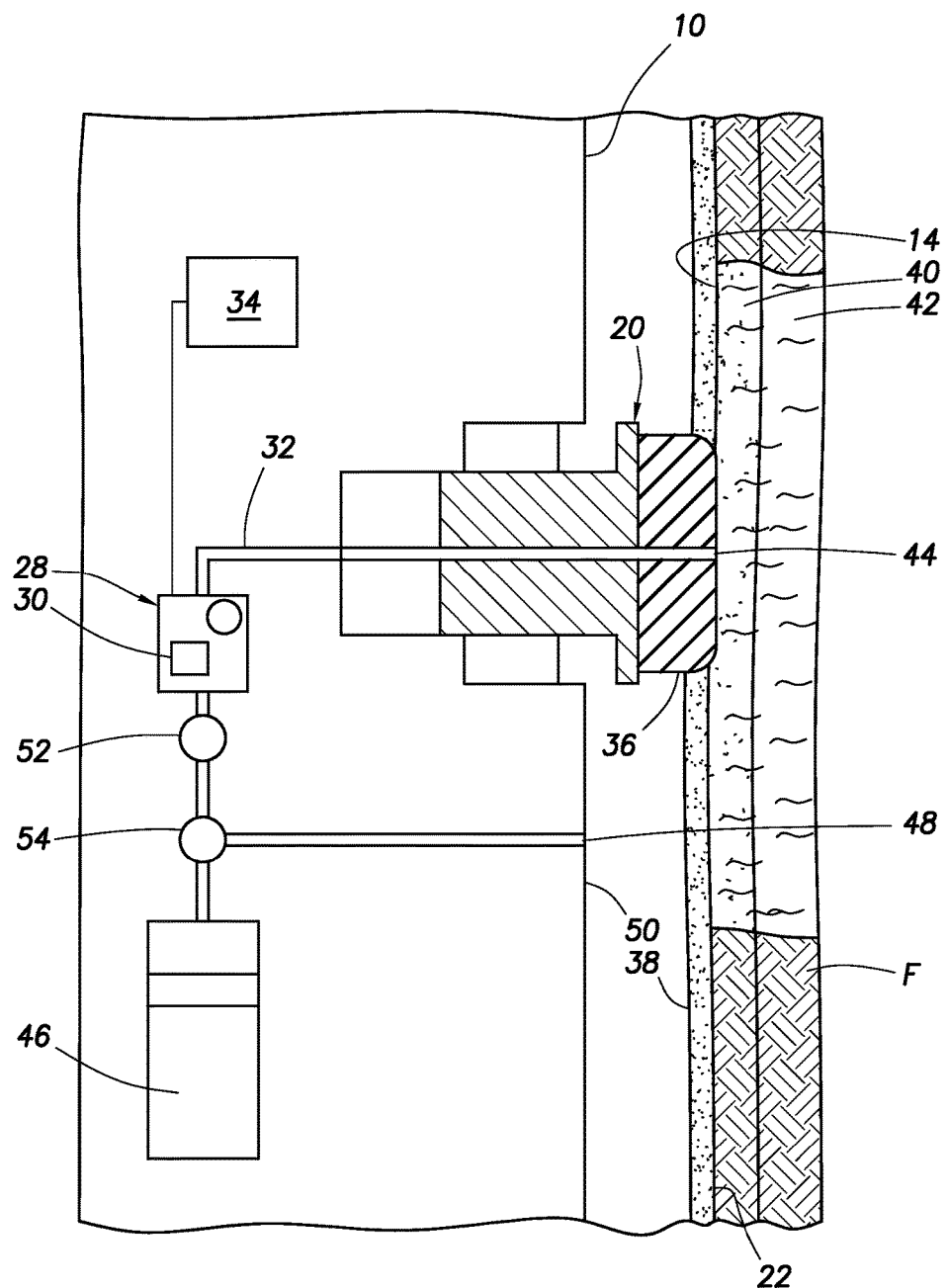
FIG. 2 depicts a schematic view of a portion of a downhole tool having a formation evaluation tool with a fluid analyzer therein in accordance with embodiments of the present disclosure.

The description that follows includes exemplary systems, apparatuses, methods, techniques, and instruction sequences that embody techniques of the inventive subject matter. However, it is understood that the described embodiments may be practiced without these specific details.

The present disclosure relates to formation evaluation involving fluid analysis. In particular, the present disclosure describes systems, apparatuses and methods for performing downhole fluid analysis and/or calibrating a fluid analyzer. A fluid analyzer with a calibrator is positionable in a downhole tool and deployable into a wellbore for analyzing fluid drawn into the downhole tool. The calibrator has a calibration fluid source that may selectively provide a calibration fluid to the fluid analyzer for providing calibration (or reference) measurements. Calibration measurements may be performed downhole in situ at downhole conditions, and compared with other calibration measurements to confirm accuracy of the fluid analyzer measurements.

'Formation evaluation' as used herein relates to the measurement, testing, sampling, and/or other analysis of wellsite materials, such as gases, fluids and/or solids. Such formation evaluation may be performed at a surface and/or downhole location to provide data, such as downhole parameters (e.g., temperature, pressure, permeability, porosity, etc.), material properties (e.g., viscosity, composition, density, etc.), and the like.

'Fluid analysis' as used herein relates to a type of formation evaluation of downhole fluids, such as wellbore, formation, reservoir, and/or other fluids located at a wellsite. Fluid analysis may be performed by a fluid analyzer capable of measuring fluid properties, such as viscosity, composition, density, temperature, pressure, flow rate, optical parameters, etc. Fluid analysis may be performed using, for example, optical sensors (e.g., spectrometers), gauges (e.g., quartz), densitometers, viscometers, resistivity sensors, nuclear sensors, and/or other fluid measurement and/or detection devices.

FIGS. 1.1 and 1.2 depict environments in which subject matter of the present disclosure may be implemented. FIG. 1.1 depicts a downhole drilling tool 10.1 and FIG. 1.2 depicts a downhole wireline tool 10.2 that may be used for performing formation evaluation. The downhole drilling tool 10.1 may be advanced into a subterranean formation F to form a wellbore 14. The downhole drilling tool 10.1 may be conveyed alone or among one or more (or itself may be) measurement-while-drilling (MWD) drilling tools, a logging-while-drilling (LWD) drilling tools, or other drilling tools. The downhole drilling tool 10.1 is attached to a conveyor (e.g., drillstring) 16 driven by a rig 18 to form the wellbore 14. The downhole drilling tool 10.1 includes a probe 20 adapted to seal with a wall 22 of the wellbore 14 to draw fluid from the formation F into the downhole drilling tool 10.1 as depicted by the arrows.

The downhole drilling tool 10.1 may be withdrawn from the wellbore 14, and the downhole wireline tool 10.2 of FIG. 1.2 may be deployed from the rig 18 into the wellbore 14 via conveyance (e.g., a wireline cable) 16. The downhole wireline tool 10.2 is provided with a probe 20 adapted to seal with the wellbore wall 22 and draw fluid from the formation F into the downhole wireline tool 10.2. Backup pistons 24 may be used to assist in pushing the downhole wireline tool 10.2 and probe 20 against the wellbore wall 22 and adjacent the formation F.

The downhole tools 10.1, 10.2 may also be provided with a formation evaluation tool 28 with a fluid analyzer 30 for analyzing the formation fluid drawn into the downhole tools 10.1, 10.2. The formation evaluation tool 28 includes a flowline 32 for receiving the formation fluid from the probe 20 and passing the fluid to the fluid analyzer 30 for analysis, as will be described more fully herein. A surface unit 34 may be provided to communicate with the downhole tools 10.1, 10.2 for passage of signals (e.g., data, power, command, etc.) therebetween.

While FIGS. 1.1 and 1.2 depict specific types of downhole tools 10.1 and 10.2, any downhole tool capable of performing formation evaluation may be used, such as drilling, coiled tubing, wireline or other downhole tool. Also, while FIGS. 1.1 and 1.2 depict the fluid analyzer 30 in a wellbore 14, it will be appreciated that the fluid analyzer 30 may be at a surface and/or downhole location at the wellsite, and/or at an offsite facility for analyzing the fluid and/or calibration of fluid analyzer 30.

By positioning the fluid analyzer 30 in the downhole tool, real-time data may be collected in situ at downhole conditions (e.g., temperatures and pressures where formation evaluation is performed) where downhole fluids are located and/or calibrations performed. Fluids may also be evaluated at surface and/or offsite locations. In such cases, the fluid analyzer 30 and/or the formation evaluation tool 28 may be positioned in a carrier transportable to a desired location. Fluid samples may also be taken to a surface and/or offsite location, and analyzed in one or more fluid analyzers, such as fluid analyzer 30. Data and test results obtained from various locations and/or with various methods and/or apparatuses may be analyzed and compared.

FIG. 2 is a schematic view of a portion of a downhole tool 10, which may be either of the downhole tools 10.1 and 10.2 of FIGS. 1.1 and 1.2. The probe 20 may be extended from the downhole tool 10 for engagement with the wellbore wall 22. The probe is provided with a packer 36 for sealing with the wellbore wall 22. Packer 36 contacts the wellbore wall 22 and forms a seal with a mudcake 38 lining the wellbore wall 22. A mud filtrate of the mudcake 38 seeps into the wellbore wall 22 and creates an invaded zone 40 about the wellbore 14. The invaded zone 40 contains the mud filtrate and other wellbore fluids that may contaminate surrounding formations, such as formation F, and a portion of clean formation fluid 42 from the formation F.

The formation evaluation tool 28 may be provided with one or more flowlines 32 for drawing fluid into the downhole tool 10 through an inlet 44 in the probe 20. While one probe 20 with one inlet 44 is depicted, one or more probes, dual packers and related inlets may be provided to receive downhole fluids and pass them to one or more flowlines 32. Examples of downhole tools and fluid communication devices, such as probes, that may be used are depicted in U.S. Pat. No. 7,458,252, previously incorporated by reference herein.

The flowline 32 extends into the downhole tool 10 to pass downhole fluid to the formation evaluation tool 28. The formation evaluation tool 28 may be used to analyze, test, sample and/or otherwise evaluate the downhole fluid.

The fluid analyzer 30 is positioned in the formation evaluation tool 28 and is coupled to the flowline 32 for receiving the downhole fluid. A sample chamber 46 is also coupled to the flowline 32 for receiving the downhole fluid. Fluid collected in the sample chamber 46 may be collected therein for retrieval at the surface, or may be exited through an outlet 48 in housing 50 of the downhole tool 10.

One or more sensors may optionally be provided to measure various downhole parameters and/or fluid properties. The sensor(s) may include, for example, gauges (e.g., quartz), densitometers, viscometers, resistivity sensors, nuclear sensors, and/or other measurement and/or detection devices capable of taking downhole data relating to, for example, downhole conditions and/or fluid properties.

Optionally, flow of the downhole fluid into and/or through the downhole tool 10 may be manipulated by one or more flow control devices, such as a pump 52, the sample chamber 46, valves 54 and/or other devices. Optionally, a surface and/or downhole unit 34 may be provided to communicate with the formation evaluation tool 28, the fluid analyzer 30, and/or other portions of the downhole tool 10 for the passage of signals (e.g., data, power, command, etc.) therebetween.

Figure 3:
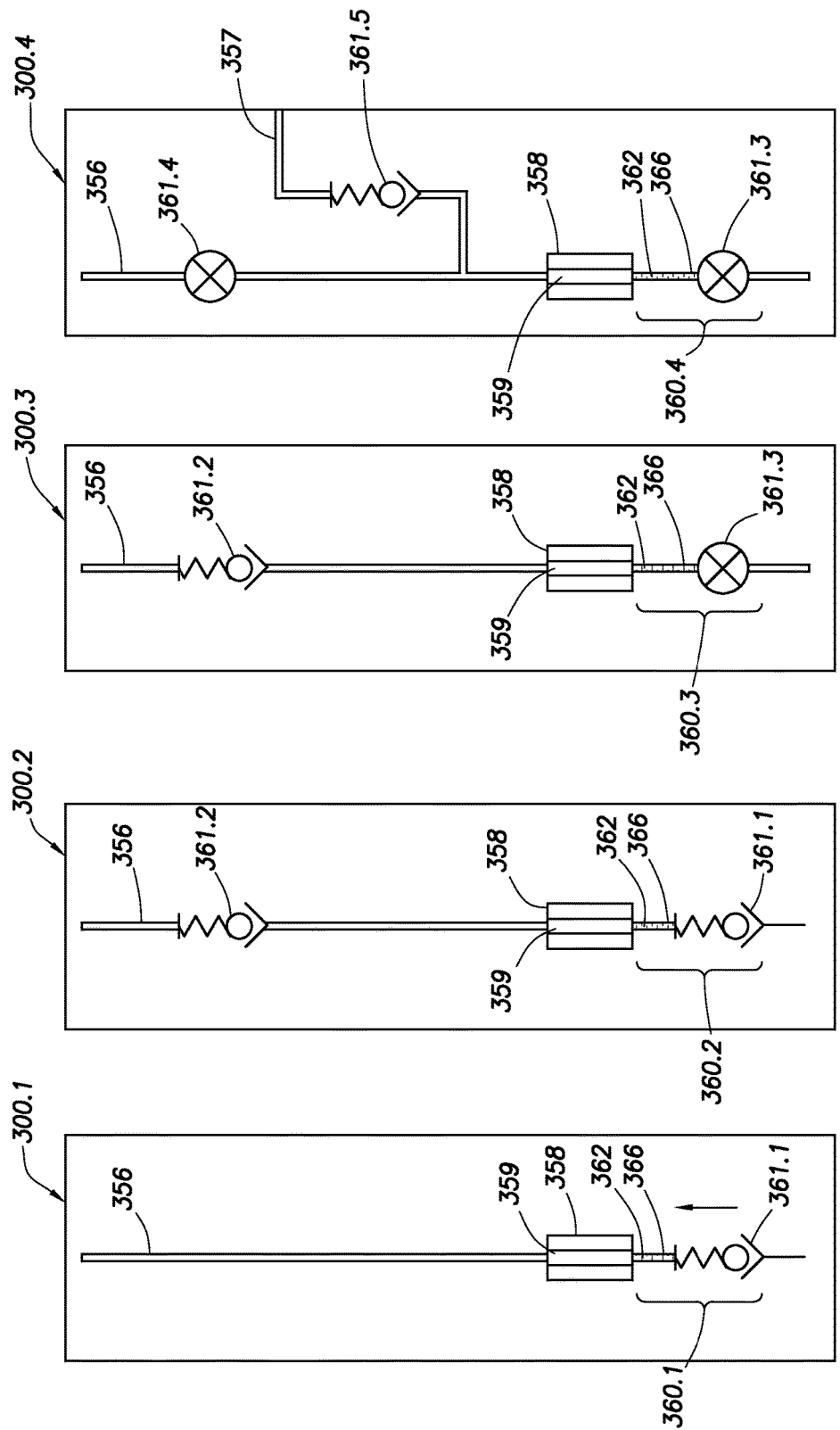
FIGS. 3.1-3.4 depict schematic views of various configurations of fluid analyzers in accordance with embodiments of the present disclosure.

FIGS. 3.1-3.4 depict various versions of a fluid analyzer 300.1-300.4 which may be used as the fluid analyzer 30 of FIGS. 1.1 and 1.2. The fluid analyzer 300.1-300.4 is provided with calibration capabilities within the downhole tool to permit calibrations to be performed anywhere the downhole tool is deployed, such as offsite, at a surface location, onsite, downhole, etc. Calibrations may be performed to confirm that the fluid analyzer 300.1-300.4 is properly measuring properties of the fluids received. Calibrations may involve measuring a known fluid to define a reference measurement. Such calibrations may be performed when and where formation evaluation is performed in real time in situ and under downhole formation evaluation conditions to assure accuracy of the measurements.

The fluid analyzer 300.1-300.4 includes a flowline 356, an optical sensor 358 and a calibrator 360.1-360.4. The flowline 356 may be the same as flowline 32 of FIGS. 1.1 and 1.2, or an additional flowline in fluid communication therewith. The flowline 356 receives downhole fluid and passes the fluid to the optical sensor 358. The calibrator 360.1-360.4 as shown in these figures includes at least one valve 361.1-361.4 and a calibration fluid source 366. The calibration fluid source 366 of these figures is in the form of a calibration flowline fluidly coupled by valve 361.1-361.4 for providing a calibration fluid thereto for measurement during a calibration operation.

The optical sensor 358 may be an optical fluid analyzer, such as MIFA™ (Modular In situ Fluid Analyzer), LFA™ (Live Fluid Analyzer), LFA-pH™ (Live Fluid Analyzer with pH), OFA™ (Optical Fluid Analyzer), and CFA™ (Composition Fluid Analyzer) commercially available from SCHLUMBERGER TECHNOLOGY CORPORATION™ (see www.slb.com), spectrometers, and/or other optical spectroscopy tools capable of measuring optical fluid properties. See also Patent/Application Nos. US2011/0061439, EP2179135 and WO2009/009409, previously incorporated by reference herein.

The calibrator 360.1-360.4 may be used to perform a calibration to confirm that the measurements taken by the optical sensor 358 are within accuracy specifications. Calibration may involve measurement by the optical sensor 358 of the calibration fluid 362 in calibration fluid source 366. To provide the calibration fluid 362 from the calibration fluid source 366 to the optical sensor 358, various arrangements, including those provided herein, may be made. For example, one or more valves 361.1-361.4 may be provided about the fluid analyzer 300.1-300.4 to selectively provide fluid flow to the optical sensor 358.

As shown in FIG. 3.1, a single check valve 361.1 is provided downstream of optical sensor 358. A calibration fluid 362 is positioned in the calibration fluid source (or flowline) 366 between the check valve 361.1 and the optical sensor 358 for selectively providing the calibration fluid 362 thereto. The check valve 361.1 retains the calibration fluid 362 in the calibration fluid source 366 and in fluid communication with a flow cell 359 of the optical sensor 358. The calibration fluid 362 in the calibration fluid source 366 may be pumped from the check valve 361.1 upstream to the optical sensor 358 as indicated by the arrow.

Additional valves may be provided, for example, to prevent dirt and debris from contaminating the calibration fluid 362 in the calibration fluid source 366. As shown in FIG. 3.2, an additional check valve 361.2 may be provided upstream of optical sensor 358 along flowline 356. The upstream check valve 361.2 may be used to selectively permit the passage of the downhole fluid to the optical sensor 358.

As shown in FIG. 3.3, the downstream check valve 361.1 of FIG. 3.2 may be replaced with a control valve 361.3. The control valve 361.3 may be opened and closed as desired to selectively permit flow therethrough. The control valve 361.3 may be activated by a solenoid valve, motor driven valve, hydraulically operated or other type of valve or controller, such as the surface and/or downhole units 34 of FIGS. 1.1 and 1.2.

As shown in FIG. 3.4, the check valves 361.1, 361.2 of FIG. 3.2 may both be replaced with control valves 361.3, 361.4 to selectively permit fluid to pass in either direction through the flowline. A secondary flowline 357 may extend from the flowline 356 between the upstream control valve 361.4 and the optical sensor 358. The additional flowline 357 may be used to provide a pressure release, for example, where a fixed volume is in the flowline 356 that may be subject to temperature changes. A check valve 361.5 is located in the secondary flowline 357 to selectively release pressure therethrough. While the check valve 361.5 is schematically depicted in the additional flowline 357, other devices, such as a rupture disc, bellows, compensating piston, and the like, may be used to release pressure.

Figure 4:
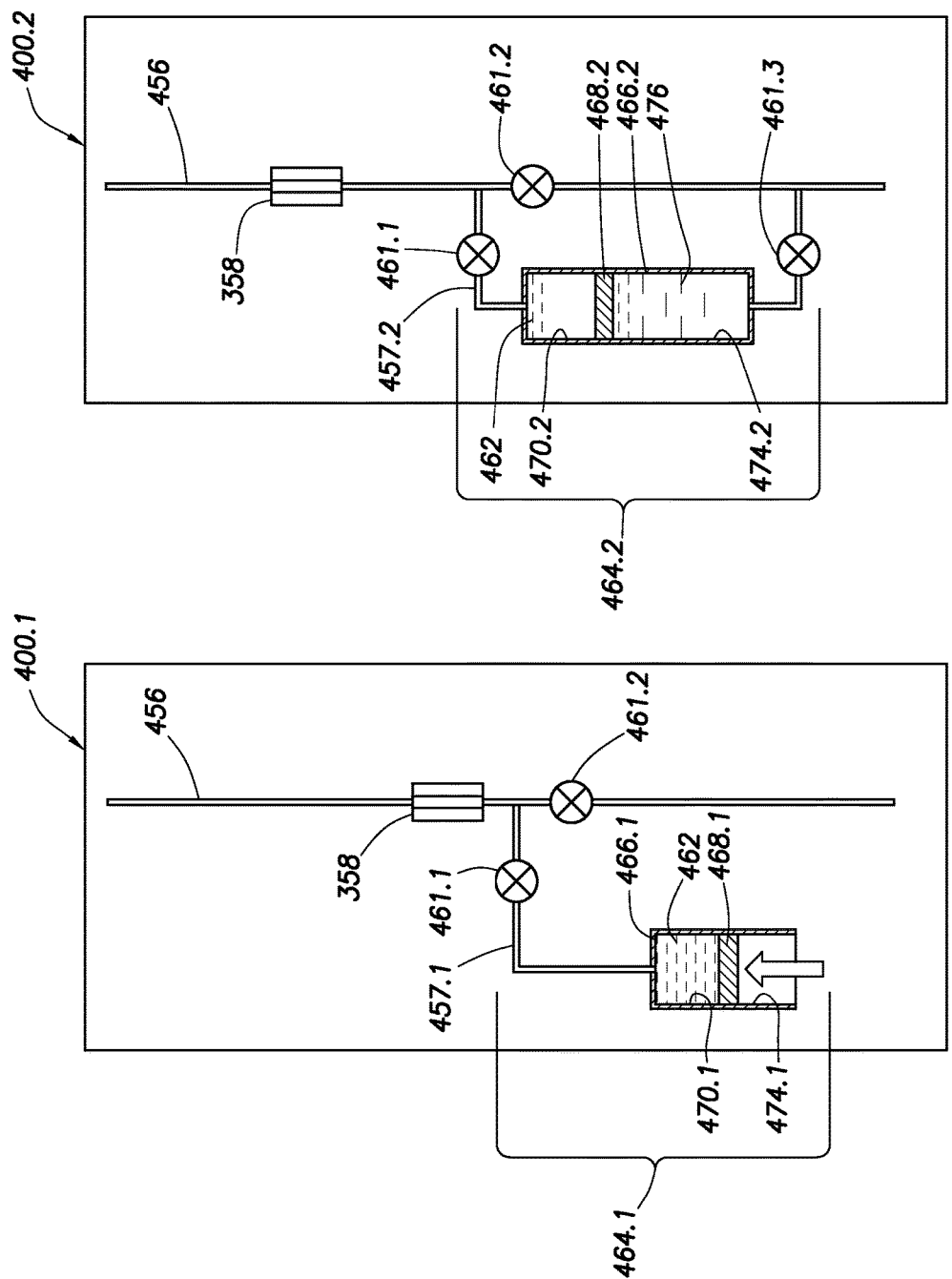
FIGS. 4.1 and 4.2 depict schematic views of various additional configurations of fluid analyzers in accordance with embodiments of the present disclosure.

FIGS. 4.1 and 4.2 depict various versions of another fluid analyzer 400.1, 400.2 which may be used as the fluid analyzer 30 of FIGS. 1.1 and 1.2. In this version, the fluid analyzers 400.1, 400.2 have calibrators 464.1, 464.2 in the form of a fluid source 466.1, 466.2 containing a calibration fluid 462. The fluid source 466.1, 466.2 may be a reservoir as shown in FIG. 4.1 or a sample chamber as shown in FIG. 4.2. These fluid source configurations may be used to provide the ability to perform multiple calibrations and/or to perform a rinsing operation, as will be described more fully herein.

The fluid analyzer 400.1, 400.2 includes a flowline 456, the optical sensor 358 and the calibrator 464.1, 464.2. The flowline 456 may be the same as flowline 32 of FIGS. 1.1 and 1.2 or an additional flowline in fluid communication therewith. The flowline 456 receives downhole fluid and passes the fluid to the optical sensor 358.

As shown in FIG. 4.1, control valve 461.2 is located downstream of the optical sensor 358. The calibrator 464.1 is fluidly coupled to the flowline 456 between the optical sensor 358 and the control valve 461.2. The calibrator 464.1 includes an additional flowline 457.1, control valve 461.1 and fluid source 466.1. The control valve 461.1 is positioned along the additional flowline 457.1 between the flowline 456 and the calibrator 464.1 to selectively permit the passage of the calibration fluid 462 from the calibrator 464.1 to the optical sensor 358. The control valve 461.1 in the additional flowline 457.1 may remain closed until such time as a calibration is desired. The valve 461.2 in the main flowline 456 may be selectively activated to permit fluid flow for sampling or other operations.

The fluid source 466.1 may be, for example, a conventional reservoir, and includes a calibration chamber 470.1 containing a calibration fluid 462. The calibration chamber 470.1 is a variable volume chamber defined by a slidable calibration piston 468.1 slidably positionable in the fluid source 466.1. A backside 474.1 of the fluid source 466.1 has a backpressure (or driving force) that may be applied thereto, for example by pressure, a drive mechanism (e.g., electromechanical, hydraulic, etc.), or other driver, as indicated by the arrow. The backpressure may urge the calibration piston 468.1 to reduce the chamber volume 470.1 and drive the calibration fluid 462 toward the optical sensor 458. The calibration fluid 462 may then be passed to the optical sensor 358 for measurement and/or to wash the optical sensor 358.

The fluid analyzer 400.2 of FIG. 4.2 is similar to the fluid analyzer 400.1, except that the calibrator 464.2 includes a fluid source 466.2 in the form of a sample chamber fluidly coupled at two positions to the flowline 456 by flowline 457.2. Flowline 457.2 is fluidly connected to flowline 456 between the optical sensor 358 and the control valve 461.2, and again downstream from the control valve 461.2 to form a flow loop thereabout. Valve 461.1 is positioned between the fluid source 466.2 and the flowline 456 as in FIG. 4.1, and an additional valve 461.3 is positioned between the fluid source 466.2 and the flowline 456 to provide selective fluid communication therewith.

The calibrator 464.2 includes a calibration piston 468.2 slidably positionable therein to define variable volume calibration fluid chamber 470.2 containing a calibration fluid 462, and variable volume buffer fluid chamber 474.2 containing a buffer fluid 476. The calibration fluid chamber 470.2 may be, for example, a conventional sample chamber used for collecting fluid samples. The buffer fluid chamber 474.2 is fluidly coupled by control valve 461.3 to a downstream end of flowline 456 for selectively venting the buffer fluid 476 thereto.

The control valves 461.1-461.3 may be selectively activated to divert pressure to the calibrator 464.2 and/or to establish fluid communication between portions of the flowline 456 to permit the calibration fluid 462 to be selectively diverted to the optical sensor 358. The calibration fluid 462 may then be passed to the optical sensor 358 for measurement and/or to wash the optical sensor 358. Optionally, borehole or formation fluid may be pumped through control valve 461.3 to the buffer fluid chamber 474.2. The control valve 461.3 adjacent buffer fluid chamber 474.2 may be used to prevent backflow from the calibrator 464.2 to avoid contamination of the fluid in the main flowline 456 from fluid pumped into the calibration fluid chamber 470.2.

While FIGS. 3.1-4.2 depict specific configurations of flowlines, calibrators, and various valves operatively connected to the optical sensor 358, various configurations may be used for selectively providing calibration fluid thereto. Embodiments shown herein are not mutually exclusive and various combinations of features may be provided. It is possible to implement any combination of these designs.

One or more formation evaluation, fluid analysis and/or calibration devices may be provided in the downhole tool. The calibrator used may optionally be filled (or refilled) at the surface with a calibration fluid. Alternatively or additionally, one or more portions of a flowline may be filled with the calibration fluid.

The calibration fluid may be provided to the optical sensor at a surface and/or downhole location at various operation conditions (e.g., temperatures, pressures, cycles, etc.), and/or using various calibration fluids. The calibration fluid may be applied at specific times, intervals, sequences and as desired to provide calibration at desired times. Calibrations may be compared with other surface, downhole, reference, test lab or other measurements by the same or different tools and/or at the same or different wellsites. The valves depicted may optionally be replaced by other flow control devices, such as a single 3-port, 2-position valve or other means.

Additional calibrations may be performed. For example, surface calibrations may be performed by passing air to an optical sensor for measurement and to monitor the measurement at various temperatures to compensate for drifts that may occur as a function of temperature. Examples of additional calibrations that may be used are provided in Patent/Publication Nos. US2011/0061439, and EP2179135, previously incorporated by reference herein.

A wide range of liquids may be selected as the calibration fluid used for the reference calibration measurement. The calibration fluid may be any fluid measurable by the optical sensor. The calibration fluid may be a fluid with a known optical density at one or more wavelengths that is within a linear response range of an optical sensor, such as a spectrometer. For example, the calibration fluid may be air, carbon tetrachloride, fluorinert, an alkane (e.g., n-heptane, n-octane, n-nonane, etc.), an oil (e.g., hydraulic oil such as J26 oil, synthetic oil, fuel oil such as diesel, oils with colorant such as diesel fuel with dye), water, nitrogen, carbon disulfide, carbon dioxide, or other known fluid with zero optical density at all wavelengths of the optical sensor. In another example, the calibration fluid may also be a liquid, such as hydrocarbon, that has a known (zero or non-zero) optical density at specific wavelengths measurable by the optical sensor.

In some cases, a cleaning fluid may be provided to clean the calibrator, fluid analyzer, formation evaluation tool, and/or other devices in the downhole tool. For example, light hydrocarbons ranging from heptanes to duodecane and above may be suitable because their optical properties may be predictable, and they can act as solvents to ensure the cleanliness of spectrometer cell windows under downhole conditions.

The calibration fluid may be selected as having a known measurement for comparison with the measurement of the optical sensor. The calibration fluid may also be selected as a fluid that does not absorb in the wavelength range of the optical sensor (e.g., spectrometer). A liquid may be used where its fluid properties (e.g., absorbance or optical density) are known at the temperature and pressure at which the reference measurement is made, and/or the intensity of transmitted light at all wavelengths of interest is within a linear response range of the optical sensor.

In an embodiment, the calibration fluid may be selected to be, for example, a liquid, such as carbon tetrachloride, that does not absorb in a wavelength range of the optical sensor. Such a liquid may have known optical properties (i.e., absorbance or optical density) in situ temperature and pressure at which the reference measurement is made, and the intensity of transmitted light at all wavelengths of interest may be within a linear response range of the optical sensor (e.g., spectrometer).

The calibration measurement may be used to compute transmittance, $T(\lambda)$ at wavelength $\lambda$, or optical density, $OD(\lambda)$, of the fluid in the flow cell. Transmittance of the fluid in a measurement cell is defined as the ratio of light intensity transmitted through the fluid in the cell, $Io(\lambda)$, to the intensity of light incident on the fluid in the cell, $Iref(\lambda)$.

$$T(\lambda) = \frac{I_0(\lambda)}{I_{ref}(\lambda)} \qquad \text{Eq. (1)}$$

-continued $$OD(\lambda) = -\log\{T(\lambda)\} = -\log\left\{\frac{I_0(\lambda)}{I_{ref}(\lambda)}\right\}$$

With certain surface calibrations, $I_0(\lambda)$ can be measured by a photodetector placed on the opposite side of the flow cell to a light source of the optical sensor. $I_{ref}(\lambda)$ can be inferred from a measurement of $I_0(\lambda)$ when the fluid in the fluid cell absorbs no light at the measurement wavelengths, i.e., the reference fluid has a transmittance of one (1), or optical density of zero (0). From Equation (1) above, the following applies:

if $T(\lambda)=1$, then $Iref(\lambda)=I_0(\lambda)$  Eq. (2)

Knowing the value of $I_{ref}(\lambda)$ measured on surface, the transmittance or optical density of a fluid downhole can be determined by measuring $I_0(\lambda)$ downhole and applying Equation (1) above.

Because the optical coupling of the light source to the measurement cell and to the photodetector may change with temperature, in the absence of the present disclosure, multiple measurements at a range of temperatures have to be made in order to apply a temperature correction to the computed value of transmittance or optical density.

Using the downhole calibration techniques provided herein, the reference intensity measurement made at the surface may be replaced with an equivalent measurement made downhole. If the reference measurement is made downhole with the optical sensor at, or close to, the operating temperature, it may not be necessary to make a separate temperature correction because the reference measurement can compensate for temperature effects.

The reference fluid may not necessarily be required to have zero optical density at the wavelengths of interest for the optical sensor. For reference measurements made at the surface, air may be used in the optical cell for the measurement. Air at atmospheric pressure is assumed to have zero optical density. While air may not absorb light in the wavelength range of an optical sensor, there may be an effect of reflection at the surfaces of the windows of the optical cell, which may reduce the amount of transmitted light compared to the level with a liquid in the cell. As a result, at some wavelengths, apparent negative optical densities may be recorded when water or hydrocarbons are monitored using the measurement with air as the reference measurement and compensations may be made.

For downhole calibrations, the optical properties of the fluid may be considered in selecting a desired calibration fluid. If ODref($\lambda$) is the optical density at wavelength $\lambda$ of the calibration fluid, and Imeas($\lambda$) is the intensity measured in a downhole reference measurement, then the value of Iref($\lambda$) to be used when computing the optical density of an arbitrary sample is given by:

$$OD_{ref}(\lambda) = -\log\left\{\frac{I_{meas}(\lambda)}{I_{ref}(\lambda)}\right\}$$  Eq. (3)

which may be rewritten as:

$$I_{ref}=I_{meas}(\lambda)\times 10^{OD_{ref}(\lambda)}$$  Eq. (4)

Data collected using the fluid analyzers of FIGS. 3.1-4.2 may be passed to a downhole or surface unit 34, and/or other onsite and/or offsite units. The units may be provided with databases, processors, controllers, transceivers, interfaces and other computer devices to collect, process, analyze, transmit, or otherwise manipulate data. The fluid analyzers and/or other sensors may have one or more channels for collecting and sending data. Data collected from the fluid analyzers and/or other sensors may be analyzed alone or in combination with other data. Data may be compared, for example, to determine the validity of the calibrations and/or the accuracy of the fluid analyzers and/or sensors. Optionally, the units may be provided with controls, alerts or other devices that may activate in response to data and/or resulting analysis.

Figure 5:
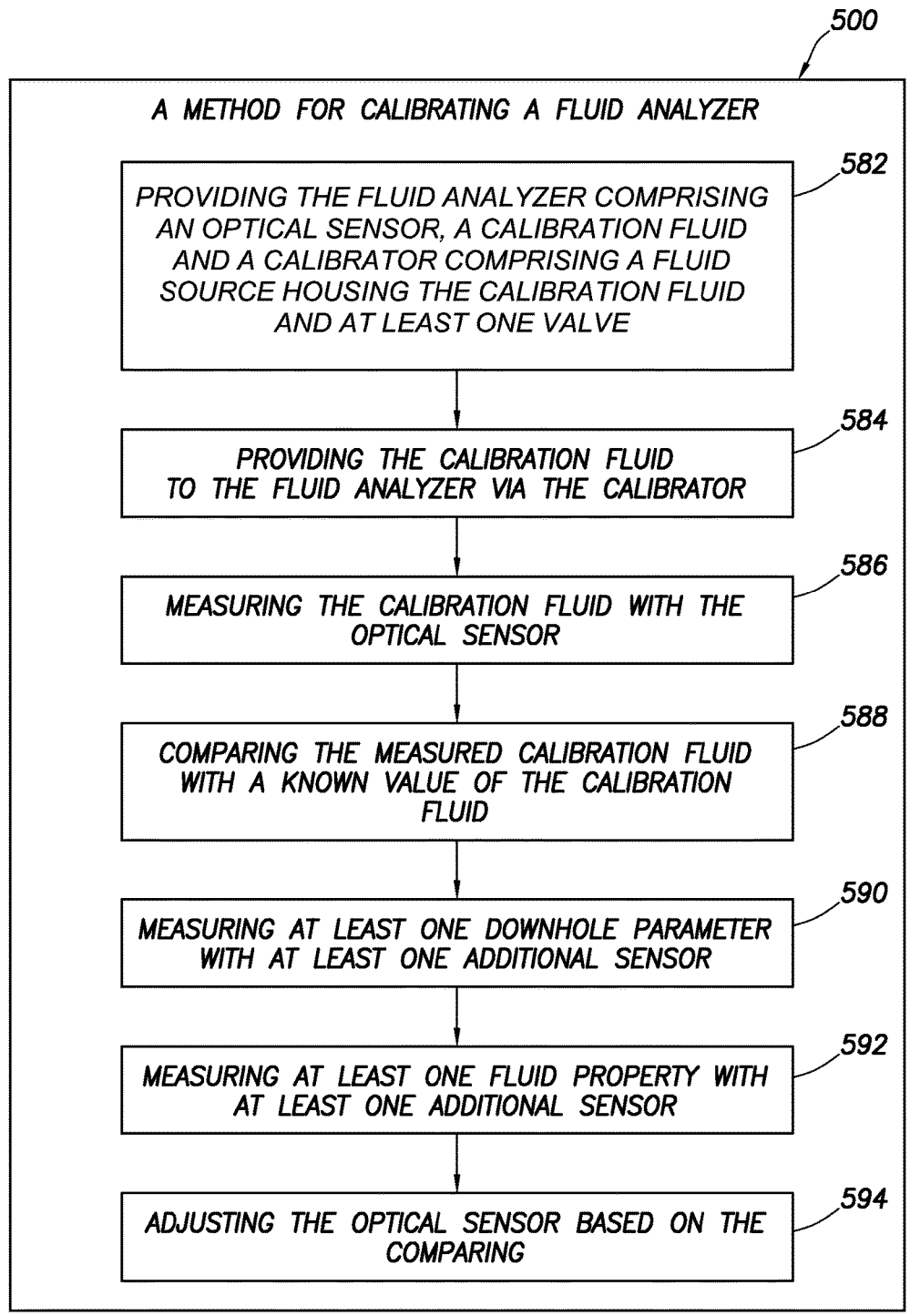
FIG. 5 is a flow chart depicting a method of calibrating a fluid analyzer in accordance with embodiments of the present disclosure.

FIG. 5 shows a flow chart of a method 500 for calibrating a fluid analyzer. The method involves providing (582) the fluid analyzer with a calibrator including an optical sensor, a fluid source and at least one valve. The method also involves providing (584) the calibration fluid to the fluid analyzer via the calibrator, and measuring (586) the calibration fluid with the optical sensor.

The method may also involve comparing (588) the measured calibration fluid with a known value of the calibration fluid, and adjusting (594) the optical sensor based on the comparing. In some cases, the method may also involve measuring (590) at least one downhole parameter with at least one additional sensor, and/or measuring (592) at least one fluid property with at least one additional sensor. The comparing (588) and adjusting (594) may be performed with the measurings (590, 592). Part or all of the method may be repeated as desired.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A fluid analyzer for a downhole tool positionable in a wellbore penetrating a subterranean formation, a downhole fluid receivable in a flowline of the downhole tool, the fluid analyzer comprising:
   an optical sensor positioned in the downhole tool to receive the downhole fluid via flow in a direction from an inlet of the optical sensor, the optical sensor comprising an optical cell to measure properties of the downhole fluid, and the optical sensor having a wavelength range for the downhole fluid;
an outlet flowline in fluid communication with the optical sensor for at least flow of the downhole fluid out of the optical sensor;
an amount of a calibration liquid that is a solvent that has a zero optical density in the wavelength range for the downhole fluid, wherein the amount is sufficient for a plurality of calibrations; and
a calibrator comprising a chamber for the calibration liquid and a drive mechanism that drives the calibration liquid from the chamber to the optical sensor via a calibration flowline coupled to the outlet flowline, wherein the calibration flowline joins the outlet flowline at a location between the optical sensor and a valve of the outlet flowline, wherein the valve is closed for flow of the calibration liquid to the optical sensor, and whereby a first measurement made by the optical sensor for a first one of the calibrations provided with a first portion of the calibration liquid by the drive mechanism, at a first downhole operating temperature of the optical sensor, is indicative of a first accuracy of the optical sensor based on a first in situ downhole physical condition of the optical sensor at the first downhole operating temperature and a second measurement made by the optical sensor for a second one of the calibrations provided with a second portion of the calibration liquid by the drive mechanism, at a second downhole operating temperature of the optical sensor, is indicative of a second accuracy of the optical sensor based on second in situ downhole physical condition of the optical sensor at the second downhole operating temperature.

2. The fluid analyzer of claim 1, wherein the calibration liquid has zero optical density the downhole operating temperature and a corresponding downhole operating pressure.

3. The fluid analyzer of claim 1, wherein the calibration liquid has an intensity of transmitted light in the wavelength range.

4. The fluid analyzer of claim 1, wherein the calibrator further comprises at least one additional valve positionable along the flowline to selectively provide the downhole fluid thereto.

5. The fluid analyzer of claim 1, wherein the optical sensor comprises a spectrometer.

6. The fluid analyzer of claim 1 wherein the drive mechanism comprises a piston that drives the calibration liquid from the chamber by reducing the volume of the chamber.

7. The fluid analyzer of claim 1 wherein the chamber is a variable volume chamber defined by a slidable calibration piston that is slidably positionable by the drive mechanism.

8. The fluid analyzer of claim 1 wherein the calibration liquid washes the optical sensor.

9. The fluid analyzer of claim 1, wherein the calibration liquid comprises carbon tetrachloride.

10. The fluid analyzer of claim 1, wherein the in situ physical conditions of the optical sensor depends on cleaning of the optical call by the calibration liquid.

11. A downhole tool positionable in a wellbore penetrating a subterranean formation, the downhole tool comprising:
a housing having a flowline receving a downhole fluid therein; and
a fluid analyzer, comprising:
an optical sensor positioned in the downhole tool to receive the downhole fluid via flow in a direction from an inlet of the flowline to a fluid inlet of the optical sensor, the optical sensor comprising an optical cell to measure properties of the downhole fluid in the flowline, and the optical sensor having wavelength range for the downhole fluid;
an outlet flowline in fluid communication with the optical sensor for at least flow if the downhole fluid out of the optical sensor;
an amount of a calibration liquid that is a solvent that has a zero optical density in the wavelength range for the downhole fluid, wherein in the amount is sufficient for a plurality of calibrations; and
a calibrator comprising a chamber for the calibration liquid and a drive mechanism that drives the calibration liquid from the chamber to the optical sensor via a calibration flowline coupled to the outlet flowline, wherein the calibration flowline joins the outlet flowline at a location between the optical sensor and a valve, wherein the valve is closed for flow of the calibration liquid to the optical sensor, and whereby a first measurement made by the optical sensor for a first one of the calibrations provided with a first portion of the calibration liquid by the drive mechanism, at a first downhole operating temperature of the optical sensor, is indicative of a first accuracy of the optical sensor based on a first in situ downhole physical condition of the optical sensor at the first downhole operating temperature and a second measurement made by the optical sensor for a second one of the calibrations provided with a second portion of the calibration liquid by the drive mechanism, at a second downhole operating temperature of the optical sensor, is indicative of a second accuracy of the optical sensor based on second in situ downhole physical condition of the optical sensor at the second downhole operating temperature.

12. The downhole tool of claim 11, further comprising a probe positionable adjacent a wall of the wellbore and having an inlet to intake the downhole fluid, the inlet fluidly coupled to the optical sensor via the flowline.

13. A method of calibrating a fluid analyzer of a downhole tool positionable in a wellbore penetrating a subterranean formation, a downhole fluid receivable in a flowline of the downhole tool, the method comprising:
providing the fluid analyzer with a calibrator, comprising:
an optical sensor positioned in the downhole tool to receive the downhole fluid therefrom, the optical sensor comprising an optical cell to measure properties of the downhole fluid in the flowline, and the optical sensor having a wavelength range for the downhole fluid;
an outlet flowline in fluid communication with the optical sensor for at least flow of the downhole fluid out of the optical sensor;
an amount of a calibration liquid that is solvent that has a zero optical density in the wavelength range for the downhole fluid, wherein the amount is sufficient for a plurality of calibrations; and
a calibrator comprising a chamber for the calibration liquid and a drive mechanism that drives the calibration liquid from the chamber to the optical sensor via a calibration flowline coupled to the outlet flowline, wherein the calibration flowline joins the outlet flowline at a location between the optical sensor and a valve, wherein the valve is closed for flow of the calibration liquid to the optical sensor, and whereby a measurement made by the optical sensor for one of the calibrations, at a downhole operating temperature of the optical sensor, is indicative of accuracy of the optical sensor based in in situ downhole physical condition of the optical sensor at the downhole operating temperature;

for a calibration at a first downhole operating temperature, providing a portion of the calibration liquid to the fluid analyzer via the calibrator and measuring the calibration liquid at a downhole location with the optical sensor to provide a measurement for the first downhole operating temperature; and for another calibration at a second downhole operating temperature, providing another portion of the calibration liquid to the fluid analyzer via the calibrator and measuring the calibration liquid at a downhole location with the optical sensor to provide a measurement for the second downhole operating temperature.

14. The method of claim 13, further comprising comparing each of the measurements to a known value of 100 percent transmittance of the calibration liquid.

15. The method of claim 13, further comprising measuring at least one downhole parameter with at least one additional sensor.

16. The method of claim 13, further comprising calibrating the fluid analyzer at a surface location using air.

* * * * *